United States Patent [19]

North et al.

[11] Patent Number: 4,614,366

[45] Date of Patent: Sep. 30, 1986

[54] NAIL IDENTIFICATION WAFER

[75] Inventors: Vaughn W. North; Richard W. Elggren, both of Sandy, Utah

[73] Assignee: EXACTident, Inc., Utah

[21] Appl. No.: 582,086

[22] Filed: Feb. 21, 1984

Related U.S. Application Data

[63] Continuation-in-part of Ser. No. 553,770, Nov. 11, 1983.

[51] Int. Cl.$^4$ ............................................. B42D 15/00
[52] U.S. Cl. .................................... 283/70; 235/375;
283/75; 283/79; 283/81; 283/901
[58] Field of Search ................. 433/229; 283/1 R, 72,
283/79, 73, 75, 76, 81, 85, 107, 101, 70, 900, 71,
904, 901; 235/375, 376, 385, 382, 449, 493;
116/114 R

[56] References Cited

U.S. PATENT DOCUMENTS

| Re. 30,594 | 4/1981 | Samis | 433/229 |
|---|---|---|---|
| 3,814,049 | 6/1974 | Hunter | 116/114 R |
| 3,831,006 | 8/1974 | Chaffin, III et al. | 235/375 |
| 3,848,112 | 11/1974 | Weichselbaum et al. | 235/375 |
| 4,164,320 | 8/1979 | Irazoqui et al. | 235/375 |
| 4,239,261 | 12/1980 | Richardson | 283/81 X |
| 4,328,978 | 5/1982 | McLaughlin | 283/75 X |
| 4,476,381 | 10/1984 | Rubin | 283/900 X |

Primary Examiner—Paul A. Bell
Attorney, Agent, or Firm—Calvin E. Thorpe; Vaughn W. North; M. Wayne Western

[57] ABSTRACT

A device and method for applying and retaining a data carrier to a living body for providing identification of the body with respect to a reference group wherein the body's external nail surface structure, the method comprising selecting a carrier suitable for attachment to the nail surface, modifying the carrier to include a unique data format and attaching the carrier at the nail surface. The data carrier comprises a thin, substantially flat carrier suitable for attachment to the nail surface and a unique data format applied to the carrier adapting the same for repeated detection. The device and method are adaptable for use within identification systems such as hospital patient identification, clinical testing and security access control environments.

33 Claims, 6 Drawing Figures

NAIL IDENTIFICATION WAFER

This is a continuation in part of application Ser. No. 06-553,770, filed Nov. 11, 1983.

BACKGROUND OF THE INVENTION

1. Field of the Invention

The present invention relates to a method and apparatus for attachment of a data carrier to an individual for the purpose of providing immediate accessability to information about his medical condition, personal identification, and other pertinent data. Note particularly, that the present invention pertains to a device and method for applying and retaining a data carrier to a living body at an external nail surface on the body.

2. Prior Art

The referenced parent application discusses prior art generally in human identification systems. The need for positive identification arises under many circumstances. Accurate identification is particularly important in circumstances where services are performed for the individual based on the identification provided. For example, in a hospital environment, the accurate identification of clinical test results with respect to a specific patient is critical. Failure to accurately identify the test results and the correct patient could result in improper diagnosis and treatment.

Currently, the method of identification of patients in a health care facility is by means of a plastic wrist band. The wrist band typically includes an embossing plate which carries the patient's name, hospital number and other relevant data for use within the hospital system. The wrist band is strapped around the patient's wrist and crimped or sealed to inhibit voluntary removal of the band prior to out processing. Clearly, the object of such identification devices is to attach a semipermanent form of ID in an accessable position on the patient's person. Accessability is critical in view of the numerous persons who interact with the patient while under hospital care. In most instances, such individuals are not personally acquainted with the patient and must rely exclusively on the wrist band for positive identification.

Despite the fact that the hospital wrist band has been a part of institutional health care for decades, the wrist band has serious deficiencies. For example, the wrist band is located over a primary site for intravenous injections. As a consequence, the comfort and well being of the patient are at some risk if the wrist band were to interfere with normal IV administrations. Similarly, the wrist band can interfere with other medical activities which are orientated at the wrist position, such as pulse counts. Those experienced with the inconvenient location of the wrist band for hospital use will understand that the disadvantages noted above for this location only partially represent the problems associated therewith.

In addition to the inconvenience of the location for the wrist band, other related problems have long existed. For example, the wrist band creates a non-sterile object which breaches the sterile field required for the operating room. Accordingly, the arms of the patient must be strapped down to prevent the wrist band from being inadvertently contacted with a sterile area. The wrist band is also a cumbersome attachment which creates discomfort for the patient, causing sweating and sometimes resulting in a rash. Because of the size differences between adults and children, multiple size bands are often required. As is well known by those working within the hospital systems, patients will remove the wrist bands when irritation is excessive.

A unique identification problem arises with respect to newborn infants. Current wrist bands are difficult to size to the infant's arm in a manner that secures it against involuntary removal. If the infants are particularly small, such as in the case of neonates, the wrist band is totally impractical and other alternatives must be developed to insure proper identification. Even with older children, the placement of the wrist band becomes a traumatic experience. In some instances, a fearful child entering a large hospital facility will literally fight to prevent the wrist band from being put in place. All these disadvantages would seem to dictate in favor of an alternative to the traditional wrist band identification system. However, because of the temporary nature of this device, the public and the hospital systems have been willing to bear the risks and inconvenience.

Other needs for temporary identification are manifold. For example, certain institutions and businesses require a security access card for entrance or access to information. Typically, this card is worn on a chain around the neck or carried in the wallet. In order to gain access, the card is shown to a security guard or other entrance personnel. Various data formats may be used to give authorization for entry, depending on the sensitivity of information or location being protected. In some instances, a photograph will suffice. In other cases, however, an electronic code imbeded in a magnetic memory field may be utilized. In all instances, however, the card is inconvenient and represents a visual tag which immediately identifies the individual with the particular institution. The users of such security cards are reluctant to remove them because of the likelihood of forgetting to put them in place when needed. Failure to remember to carry the required security card frequently results in wasted time and effort as the employee must retrace steps to secure his access card.

These requirements for temporary identification are only two examples of many different fields where a more convenient form of identification is needed.

OBJECTS AND SUMMARY OF THE PRESENT INVENTION

It is an object of the present invention to provide a means for temporary identification of a living body wherein the identification is attached directly to the body in a location which is both convenient and secure.

It is a further object of the present invention to provide an identification device for use within a hospital system.

A still further object of the present invention is the provision of a hospital identification device which can be useful in coordinating patient identification with test specimens, hospital medical records and billing systems.

An additional object of the present invention is to provide an identification device for use as part of a security access procedure wherein persons having the identification device are permitted entry while others are barred access.

These and other objects are realized in an identification process which involves a method for applying, retaining and detecting a data carrier on a nail surface of a living body. The data carrier functions as an identification device for use with respect to a reference group such as patients within a hospital, employees requiring security clearance for entrance or access to information, and similar circumstances where the identification of the wearer needs to be verified. The process involves (i) selecting a carrier suitable for attachment to a nail surface on the body, such as a finger or toe nail, (ii) encoding the carrier to include a unique data format for the body with respect to its reference group, (iii) permanently or semipermanently attaching the carrier at the nail surface and (IV) scanning the data format for detection. The data format applied should preferably be capable of detection by non-invasive, passive means which do not alter the capability for repeated detection. The subject process is specifically applied to hospital environments, security access situations and related circumstances where individual identification is frequently required.

The data carrier for fixation at the nail surface comprises (i) a thin, substantially flat carrier suitable for attachment to the nail surface, (ii) a unique data format applied to the carrier, and (iii) adhesive material for attaching and retaining the carrier to the nail until it is to be purposefully removed.

The dominant benefit of the nail identification wafer is its secure attachment to a nail surface of the body which may be easily accessed by reading devices to make positive identification. The nail surface provides other advantages over the prior art. It may be sterilized, quickly scanned by reading devices, and can carry sufficient information to allow emplacement of additional data which may be relevant for any particular application. Such additional data might include blood type, allergies and other medical information in a hospital care system, or particular restrictions for an individual relating to security access levels. Other objects and features of the present invention will be apparent to those skilled in the art, when taken in combination with the following detailed description and detailed drawings.

DETAILED DESCRIPTION OF THE DRAWINGS

Figure 4:
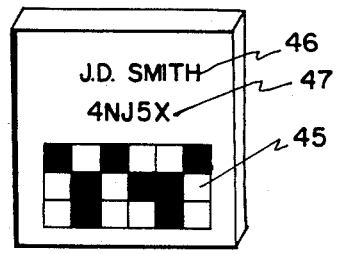

FIG. 4 discloses an alternate embodiment of the wafer with a differing data format.

Figure 5:
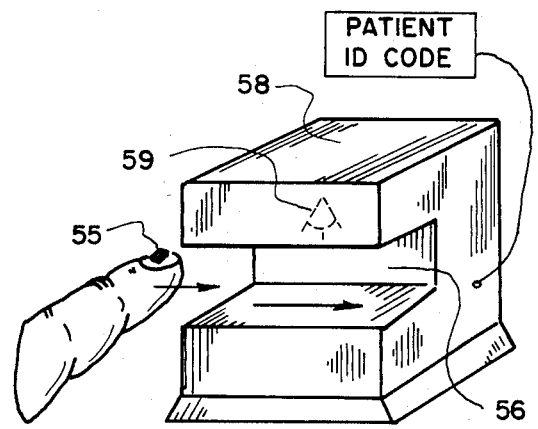

FIG. 5 illustrates a magnetic wafer with reading system.

Figure 6:
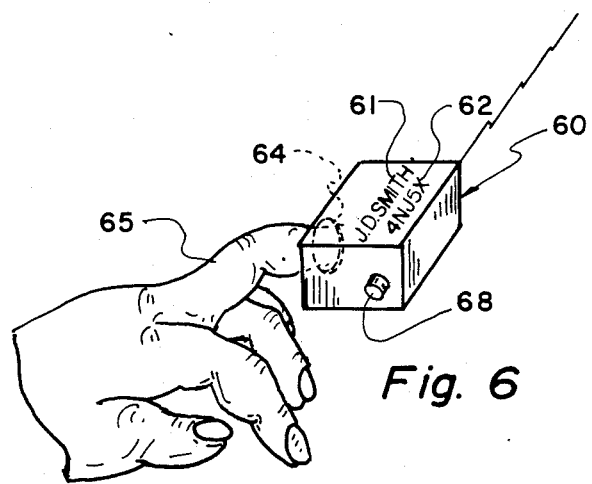

FIG. 6 depicts a perspective view of an optical reading device which fits over the end of a finger containing the nail wafer.

DETAILED DESCRIPTION OF THE INVENTION

Referring now to the figures:

A nail wafer 10 is attached at its back surface 14 to a fingernail surface 11. The finger selected for use is the ring finger 12 of the left hand 13. It will be apparent that other nail surfaces of the hand or foot could be selected. Examples of factors influencing this choice include circumstances and degree of required accessibility for third parties, exposure of nails to abrasive conduct, type of detection or reading devices to be used with the wafer, nail size, nature of information or data to be contained on the wafer and purposes for data wafer use. Other factors will become more apparent with respect to each particular application considered for this type of identification.

Figure 1:
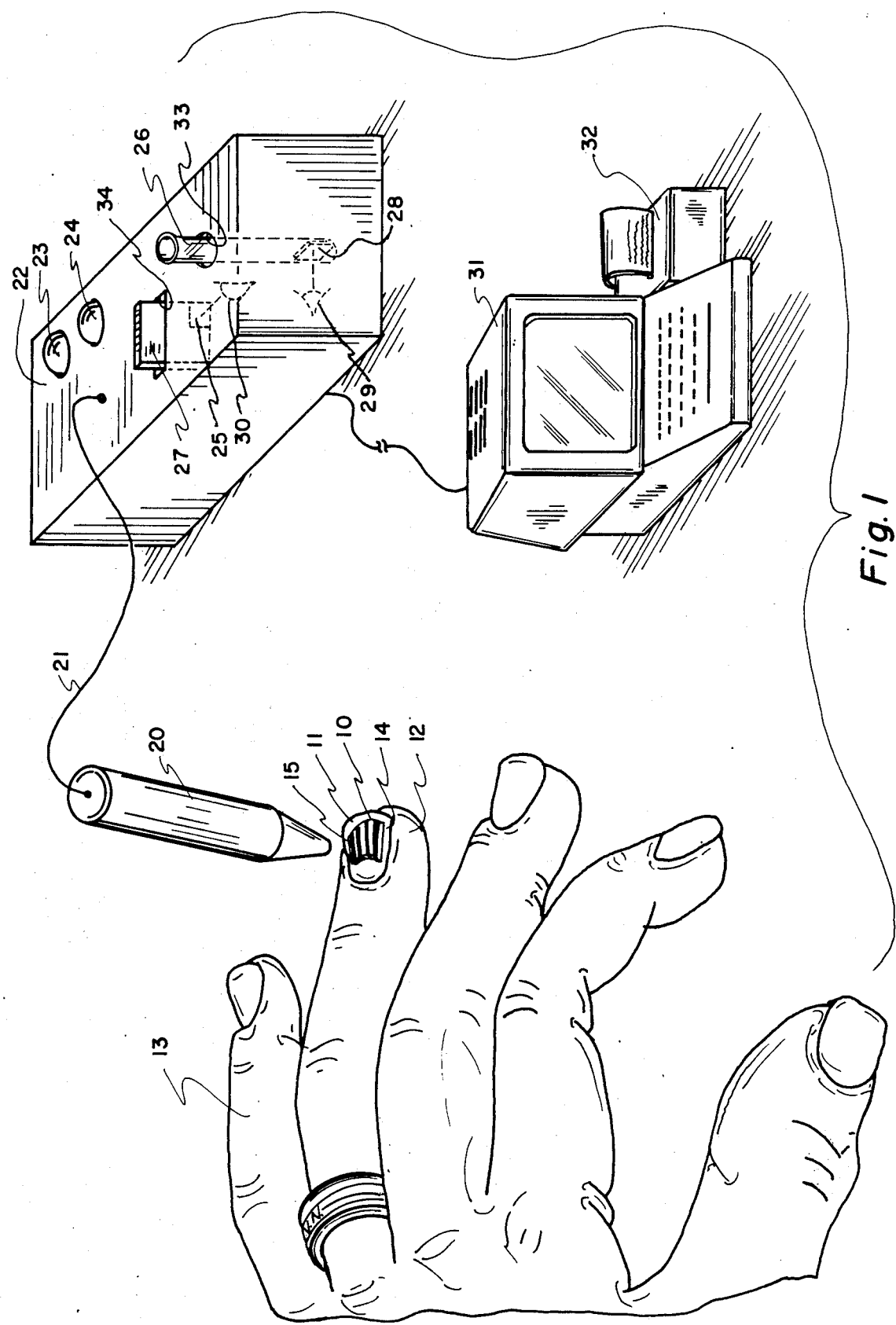
FIG. 1 represents a graphic layout of a nail identification wafer within a system for hospital identification.
Figure 2:
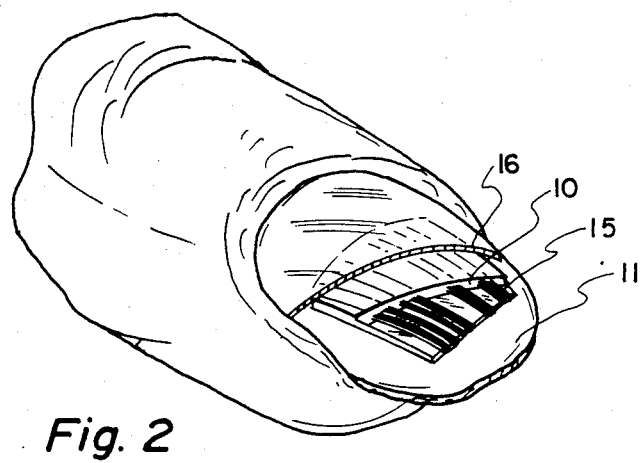
FIG. 2 depicts a partial end view of the nail wafer of FIG. 1.
Figure 3:
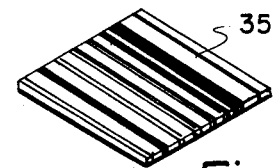
FIG. 3 illustrates another embodiment of the wafer with a machine readable bar code.

The data wafer comprises a thin, substantially flat carrier 10 suitable for attachment to the nail surface 11. FIGS. 1 and 2 depict a 4 mil Mylar film as the carrier material; however, many materials are suitable because of the insensitive nature of the nail surface. Other considerations involve the ability of the material to retain its form and function under varying temperatures and gradients, exposure to cleaning materials and compounds which can forseeable contact the wafer, and factors relating to the retention of a data format to be discussed hereafter.

In order to ensure secure attachment to the nail surface, wafer length and width dimensions should not exceed the size of the nail to which it is attached. In most applications wafer size will be significantly smaller than the exposed nail surface to facilitate positioning of a standard wafer configuration on numerous differing nails. For example, a wafer 70 mils square can fit on a fingernail of both adult and child. If wafers are too large for regular emplacement on the fingernail, a toenail will provide greater surface area.

A unique data format 15 is applied to the carrier 10 such that the data format is (i) capable of detection as a unique identification for the body to which it is attached, and (ii) capable of detection by noninvasive, passive means which do not alter the capability for frequent readings. Repeated detection is preferably and will become more apparent with following descriptions of uses of the data wafer within a hospital or security access system. In short, the data format and carrier comprise an integral device which must provide accurate readout over an extended period of time and under frequent use. In view of this, references to permanent attachment will be found hereafter. The meaning of permanent as used herein will generally refer to a fixation of the wafer at a nail surface for the purpose of retaining the wafer in place until it is to be purposefully removed. This may extend for a period of hours, weeks or months, depending upon the function of the wafer.

The selection of data format will depend upon the nature of detection or reading equipment to be used. This is usually a function of the system within which the ID wafer is to operate. In a hospital environment where automation is the objective, a machine readable format 15, 35, 45 or 55 would be desired. Under other circumstances, however, less sophisticated data formats may be acceptable. With the use of a magnification reader 60 as shown in FIG. 6, mere name 61 and/or reference code 62 may be adequate.

The data format illustrated in FIG. 5 comprises a wafer with magnetic memory. This wafer permits detection by a magnetic reading device 58 which detects and interprets the encoded data format via a reading head 59 as the wafer 55 passes through a reading slot 56. The output may be a patient ID code, or it may include a continuously updating data file. For example, patient medical files may be carried on the nail wafer by means of ROM chips which can be inductively coupled to a data encoder-decoder device 56.

The bar code format 15 illustrated in FIGS. 1 and 2 is applied photographically to the underside of the Mylar film adjacent the nail surface 11 and is oriented for proper readout.

Standard techniques for fabrication of the illustrated bar code are available within the photography industry.

The system can be automated by forming the required data format on a screen, photographing the screen and reducing it to the appropriate wafer size. Such techniques can be applied for immediate fabrication of data wafers for a particular individual. By placing the data format 15 on the under side of the film 10, it is protected from abrasive contact. In a security setting, a computer controlled fabrication procedure would allow frequent changing of the data format to impede attempts to counterfeit the system.

Such procedures may be used to develop bar code formats, or checkerboard code 45 which is capable of greater data entry. Furthermore, a custom order procedure as outlined above would enable the emplacement of the individual's name 46, as well as an alphanumeric code 47 for greater accuracy. The code, for example, could represent the name, but could also include self correcting or error checking parameters for inputing into a computer terminal. It will be apparent to those skilled in the art that numerous other data format and-/or fabrication methods could be employed to implement the subject invention.

As an illustration of one method of production, the following procedures were used. First, several access code numbers were generated, using an error detection/correction program. A generated access number was then matched to a name, and the name and access number were graphically reproduced in 24 point type. This graphic format was then photo-reduced 20 times on a 4 mil Mylar black and white film. To protect the emulsion from any tendency to dissolve the image, a protective coating of clear Krylon TM spray was administered.

Emplacement of the wafer at the nail surface is most easily accomplished by use of an adhesive. In addition, a coat of sealant 16 may be applied over the top of the wafer. Numerous clear polymers are available, including clear fingernail polish. Removal of the sealant is easily accomplished with an acetone based polish remover or other appropriate solvent. The polymer coating operates to protect the wafer from damage and also inhibits premature removal. Where a magnetic data format is used, the sealant may be colored to match other nails in appearance for cosmetic reasons.

The data format may be detected by numerous devices. FIG. 1 illustrates the use of an optical bar scanning probe 20 which converts the code into pulsed output as the scanner head traverses the bar code. This output is carried over the connecting lead 21 to a program source 22 which converts the pulsed code to a particular identification format.

If the system is adapted for use within an identification process, the method of practice further includes the step of entering the detected data format 15 into an automated reference file 31 such as a computer or comparable data processing system. This reference file 31 stores the data format for subsequent comparison with the data format contained 15 on the nail.

For example, if the identification process were applied to a group of employees to be given restricted access to information, appropriate wafers would be applied to the nail. The data format would then be entered into the reference computer 31 with proper instructions for allowing access of the wearer upon a valid scan. At some future time when the employee desires security clearance, the data format 15 is again scanned by the probe 20. The output is evaluated by the computer 31 and a determination of true identity is made. Obviously, other password requirements can be added to increase the reliability of the process. A similar system can be developed for identifying members of a reference group for the purpose of giving access to certain benefits. For example, fraud within the distribution of government assistence could be reduced by requiring the use of a data wafer (cosmetically unnoticable) which automatically verifies the entitlement of the wearer and keeps track of the amount of assistence taken in a given period.

In both examples above, verification of identity is given visually by a green light 23. Improper data would be shown by a red light 24. Obviously, other more sophisticated systems are envisioned, such as a machine activated control gate which opens for security access to restricted locations upon ID verification.

The subject invention is ideally suited for use within a medical care facility such as a hospital, care center, nursing home, etc. Data wafers could easily be emplaced during admission procedures. In fact, a sheet of adhesive-backed wafers could be assigned to the patient, with one being adhered to the nail, another to the medical file, and the remaining being given to the patient for use within the hospital. In addition to the identification process outlined above, the data wafer can be used to ensure proper identification for clinical test results. This is illustrated with the comparison devices included within element 22.

For example, if certain blood tests are to be conducted for a given patient, the attendant taking the blood specimen would bring the required container 26 and test slides 27 to the patient's location. Adhesive data wafers would be obtained from the patient and applied to the container 26 and slide 27. The attendant would then use a device such as shown as item 22 in FIG. 1, to verify the proper identification of the slide and tube. This would be done by inserting the tube in an appropriate receptacle 33 such that the wafer 28 which was applied to the tube, is in a reading position in view of a scanner 29. When the system is activated, the data wafer 28 is scanned for identification. The attendant then uses the scanning probe 20 to imput the data format from the nail wafer 10. A comparator circuit within 22 identifies whether the data formats on the nail 11 and tube 26 are identical. A green light 23 confirms the match. The same procedure is applied to the slide 27 with its attached data wafer 25. The slide is inserted into an appropriate receptacle 34 and the wafer 25 scanned 30 for comparison with the data format 15 on the nail 11. Here again, a green light 23 confirms the proper identification of the test slide, whereas a red light 24 alerts the attendant to error.

Although the comparator unit 22 is shown coupled to the reference computer 31, it will be apparent to those skilled in the art that item 22 could be a portable comparator which functions only to confirm identify between the patient and test specimens and slides used at the patient's location. The crucial step in identification within the hospital environment is the labelling of test specimens and test slides with proper patient identification. By use in the present system, test slides and specimens do not leave the patient's location until accurate identification has been confirmed.

In the clinical test application, typical procedures within the hospital require the removal of the tube 26 with the contained patient specimen and, test slides 27 to a laboratory to obtain the test results. Within the laboratory environment, the same comparator device 22 can be used to ensure accurate recording of the test sequence and results. For example, the tube 26 is inserted in the receptacle 33, receiving an appropriate data format scan. A test slide 27 has been inserted into receptacle 34, and a green light verifies the identify of the respective data formats. The lab technician is now prepared to apply a patient specimen from tube 26 onto the test slide or plate 27 to secure the test results.

The same data wafer attached to the test slide 27 can be automatically accessed for introduction of test results into the computer file 31. Identification of the patient can be programmed for automatic entry upon insertion of the slide 27 into a scanning device, such as comparator 22. The attendant can then manually type in the test results and receive the printed test report from an on-line printer 32. Where automated test slides are available, the whole process can be activated by insertion of the slide into the test monitoring equipment, with automatic entry of test results and patient identification into the computer memory 31. In this case, there is no room for manual error since all entries are activated by machine read codes. Furthermore, each stage of data entry can be crossed checked against the original data format on the test slide for a verification.

The clinical system can be further automated by using the data format on the test slide to activate patient billing records. Charge codes can be automatically entered into the computer file 31 by a preprogrammed designation on the test slide, or they can be manually entered to designate the type of charge to be recorded against the patient bill file. All other aspects of the billing sequence would be automatically triggered by scanning the data format representing the patient identification within the hospital system.

In addition to providing automatic reporting of test results and initiation of billing charges, the subject data wafer can be used to track the patient through the medical facility. For example, all patient activities which represent a health risk, a billable activity or an entry into the medical file can require activation by scanning the data wafer on the patient's nail. Imput from this scan is transferred to the central computer for the hospital, automatically recoding the nature of activity to which the patient is subjected. For example, as a patient enters physical therapy, the scan device would identify his location, date and time and would activate any charges to his bill file. By utilizing this method, a chronological record of a patient's activities and contacts throughout the hospital system is permanently recorded in the computer.

As a convenience item, a portable scanning device such as illustrated in FIG. 6 can be provided. This portable scanner 60 has an opening 64 which allows the patient to insert his finger 65 into a receptacle. Mere insertion of the finger may activate the appropriate scanning procedure to identify the patient from his data wafer. This identification can be shown on a screen 66 for visual readout by the attendant or it can be electronically scanned and passed into a memory module within the device 60 or telemetered to a local receiving station. By utilizing this device, an attending nurse can come in and identify the patient without turning on room lights by inserting the appropriate finger into the reader and depressing a screen-light button 68 to project patient name 61 and alphanumeric identification codes 62 onto the screen 66. The data wafer and format illustrated in FIG. 6 is the same data format as shown in FIG. 4. The name code 46 merely represents the patient's name for direct visual detection. For example, a simple magnification screen with a light source would enable a nurse to identify the patient by name in a manner shown in FIG. 6. The alphanumeric code 47 enables the incorporating of additional patient information which might be useful within the hospital environment. This alphanumeric code is capable of machine scanning or automated imput, for example to confirm other information of the data wafer or to access the computer system. The two dimensional bar code system shown as item 45 has been included as a second identification backup. These systems can be used in combination or separately.

Numerous scanning devices are capable of converting the data formats 45 and 47 into a useful data medium for electronic comparisons. For example, an electronic reader utilizing a Micron Technologies IS32 Optical Ram is capable of use within a detection system. Other devices and embodiments for detection will be apparent to those skilled in the art. Accordingly, it is to be understood that the examples disclosed herein are not to be construed to limit the claims which follow, which define the scope of applicant's invention.

We claim:

1. A method for identifying persons entitled to access to restricted areas or information comprising the steps of:
   a. selecting a carrier suitable for attachment to a fingernail or toenail surface of the person;
   b. encoding said carrier with a unique data format which authorizes access for the person to the area or information for the person;
   c. permanently attaching the encoded carrier at a nail surface of the person;
   d. scanning the nail surface for detection of the data format; and
   e. comparing the scanned data format with an access code for determining if access is proper.

2. A method for identifying persons entitled to access to group benefits such as medical care, insurance coverage, social services, welfare assistance, and similar privileges limited to qualified persons, said method comprising the steps of:
   a. selecting a carrier suitable for attachment to a fingernail or toenail surface of the person;
   b. encoding said carrier with a unique data format which authorizes access to a selected benefit for the person;
   c. permanently attaching the encoded carrier at a nail surface of the person;
   d. scanning the nail surface for detection of the data format; and
   e. comparing the scanned data format with reference code for determining if access is proper.

3. An identification system for providing short term identification of a body having surface nail structure, said system comprising:
   a. a thin, substantially flat carrier attached to the nail surface, said carrier having width and length dimensions less than the exposed width and length of the nail to which the carrier is attached;
   b. a unique visual data format encoded on the carrier and providing identification information with respect to the attached body;
   c. means for attaching and retaining the carrier to the nail surface until it is to be purposefully removed; and
   d. a reading device for visual observation of the data format on the carrier, said reading device including (i) a dislay window for providing a visual display of the data format, (ii) means for optically transmitting the data format from the carrier to the window and (iii) means for positioning the nail surface with carrier at the transmitting means.

4. A system as defined in claim 3, further comprising means for automatically activating the reading means upon proper positioning of the nail at the reading means.

5. A method for identifying a body with respect to a reference group wherein the body has external nail surface structure, said method comprising the steps of:
   a. selecting a carrier suitable for attachment to the nail surface;
   b. encoding said carrier with a unique data format for the body with respect to its reference group;
   c. permanently attaching the carrier to the nail surface;
   d. scanning the nail surface for detection of the data format.

6. A method as defined in claim 5, further comprising the step of sealing the carrier within a protective coating to the nail surface.

7. A method as defined in claim 5 wherein the encoding step more particularly comprises the step of encoding the carrier with a visible data format capable of optical detection.

8. A method as defined in claim 5, wherein the encoding step more particularly includes the step of encoding the carrier with a machine readable code capable of detection by an automated scanning means.

9. A method as defined in claim 5, further comprising the step of entering the detected data format into an automated reference file to provide an independently retrievable record of the data format for subsequent comparison with the data format contained on the nail.

10. A method as defined in claim 9 further comprising the steps of:
    a. detecting the data format on the nail subsequent to its being entered into the reference file,
    b. comparing the detected data format with the reference file, and
    c. signaling whether the respective detected and referenced data formats are the same or are dissimilar.

11. A method for identification as defined in claim 5, wherein the carrier comprises a thin, flexible wafer no larger than the nail surface and is adapted on one side with means for adhering the wafer thereto.

12. A method of identification as defined in claim 5, wherein the carrier comprises a thin, magnetic wafer no larger than the nail surface and is adapted on one side with means for adhering the wafer thereto, said wafer including means for magnetic encoding of the data format therein.

13. A method as defined in claim 5, further comprising the step of applying a color coating and texture which substantially resemble the appearance of other nails in their normal state, the data format being visually unnoticeable, but detectable for purposes of identification.

14. A method of identifying a patient, patient specimens, records, and related information within a health care institution comprising the steps of:
    a. selecting a carrier suitable for attachment to a fingernail or toenail surface of the patient;
    b. encoding said carrier with a unique data format for the patient;
    c. permanently attaching the encoded carrier at a nail surface of the patient;
    d. scanning the nail surface for detection of the data format;
    e. entering the detected data format into a reference file to provide an independently retrievable record of the patient identification for subsequent comparison with the data format attached on the nail.

15. A method as defined in claim 14, further comprising the steps of:
    a. preparing a plurality of carriers having the unique data format of the patient;
    b. attaching at least one data carrier to a test specimen container, plate or record relating to the patient; and
    c. comparing the data carrier attached to the test specimen container, plate or record with the reference file to verify correct correlation of tests and records with patient identity.

16. A method as defined in claim 15 comprising the more particular step of preparing transferable labels as the plurality of data carriers for attachment to the containers, plates or records, each label having the unique data format representing patient identification.

17. A method as defined in claim 15, wherein test specimen containers, plates, or records for use with the patient are labeled at the patient location with a patient code comprising the data format, said method further comprising the step of comparing the labeled data format with the data format on the patient nail to verify proper identification of the test specimen containers, plates or records prior to subsequent processing thereof at laboratory or other locations removed from the patient.

18. A method as defined in claim 17, further comprising the step of automatically transferring and recording test results into a data file by means of the patient code contained on the test container, record or plate, said code being machine scanned for automatic input into a recording means which compares the inputed code with a set of reference codes representing patients within the institution.

19. A method as defined in claim 17, further comprising the step of automatically transferring and recording test results into a patient billing file by means of the patient code contained on the test container, record or plate, said code being machine scanned for automatic input into a recording means which compares the inputed code with a set of reference codes representing patients within the institution.

20. An identification system for providing short term identification of a body having surface nail structure, said system comprising:
    a. a thin, substantially flat carrier attached to the nail surface, said carrier having width and length dimensions less than the exposed width and length of the nail to which the carrier is attached;
    b. a unique data format encoded on the carrier and providing identification information with respect to the attached body;
    c. means for attaching and retaining the carrier to the nail surface until it is to be purposefully removed;
    d. a scanning device for detecting the data format on the carrier, including means for positioning the device over the nail; and
    e. transmission means for sending the detected data format to a reference file for comparison with related information.

21. An identification system as defined in claim 20, further comprising signal means coupled to the scanning device for providing positive or negative results of identification in response to input from the scanning device.

22. An identification system as defined in claim 20, further comprising a plurality of carriers which include the same data format, at least one of the carriers being attached to the nail, the remaining carriers including means for fixation to other surfaces to be identified in connection with the nail wafer.

23. A data carrier for fixation at a fingernail or toenail surface of a body for providing identification thereof with respect to a reference group, said data carrier comprising:
   a. a thin, substantially flat carrier attached directly to the nail surface and having width and length dimensions less than the exposed width and length of the nail to which it is attached;
   b. a unique data format encoded on the carrier and including information relating to the identity of the individual to which the carrier is attached; and
   c. a means for attaching and retaining the carrier at the nail surface until it is to be purposefully removed.

24. A data carrier as defined in claim 23, wherein the carrier comprises a thin sheet of film which has the data format applied at a surface thereof.

25. A data carrier as defined in claim 24 wherein the data format is applied at the film surface positioned adjacent the nail surface and wherein the data format is oriented for detection through the exterior surface of the film, thereby adapting the film as a protective covering for the data format.

26. A data carrier as defined in claim 23 wherein the data format comprises a visible data form capable of optical detection.

27. A data carrier as defined in claim 23 wherein the data format includes a machine readable code capable of automatic detection by a scanning means.

28. A data carrier as defined in claim 23, wherein the data format includes patient identification information for use within a medical care institution.

29. A data carrier as defined in claim 28 wherein the data format includes coded information identifying special medical information such as blood type, allergies and special conditions relating to the patient wearing the wafer.

30. A data carrier as defined in claim 23, wherein the data format and carrier include security access information for use as security clearance for obtaining access to restricted information or locations.

31. A data carrier as defined in claim 23, wherein the carrier comrises a thin, magnetic wafer no larger than the nail surface and adapted to carry a data format capable of machine detection.

32. A method of identifying persons entitled to access to restricted areas or information comprising the steps of:
   a. selecting a carrier suitable for attachment to a fingernail or toenail surface of the person;
   b. encoding said carrier with a unique data format;
   c. permanently attaching the encoded carrier at a nail surface of the person;
   d. scanning the nail surface for detection of the data format;
   e. entering the detected data format into a reference file to provide an independently retrievable record for subsequent comparison with the data format attached on the nail.

33. A method for determining access rights of a person to a restricted area or controlled information as defined in claim 32, further comprising the steps of:
   a. scanning the person's nail surface for detection of the data format prior to permitting access; and
   b. comparing the scanned information with the reference file or other comparable authority for access.

* * * * *